United States Patent [19]

Drent et al.

[11] Patent Number: 5,158,921
[45] Date of Patent: Oct. 27, 1992

[54] CARBONYLATION CATALYST AND PROCESS

[75] Inventors: Eit Drent; Petrus H. M. Budzelaar; Willem W. Jager, all of Amsterdam, Netherlands

[73] Assignee: Shell Oil Company, Houston, Tex.

[21] Appl. No.: 486,566

[22] Filed: Feb. 28, 1990

[30] Foreign Application Priority Data

Mar. 3, 1989 [GB] United Kingdom ............... 8904860
Feb. 5, 1990 [GB] United Kingdom ............... 9002508

[51] Int. Cl.$^5$ .......................................... B01J 31/00
[52] U.S. Cl. ............................ 502/167; 560/97; 560/114; 560/207; 560/232; 560/233; 562/406; 562/497; 562/512
[58] Field of Search ........................................... 502/167

[56] References Cited

U.S. PATENT DOCUMENTS

| | | | |
|---|---|---|---|
| 3,887,595 | 6/1975 | Nozaki | 260/410.6 |
| 4,257,973 | 3/1981 | Mrowca | 260/410.9 |
| 4,739,109 | 4/1988 | Drent | 560/207 |
| 4,739,110 | 4/1988 | Drent | 560/207 |
| 4,786,443 | 11/1988 | Drent et al. | 260/549 |
| 4,859,764 | 8/1989 | Drent et al. | 528/392 |

FOREIGN PATENT DOCUMENTS

| | | |
|---|---|---|
| 259914 | 3/1988 | European Pat. Off. |
| 0271144 | 6/1988 | European Pat. Off. |
| 282142 | 9/1988 | European Pat. Off. |

OTHER PUBLICATIONS

New Contractive Coupling Procedure. Convenient Phosphorus Expulsion Reaction, American Chemical Society (1978) pp. 5567-5568.

Primary Examiner—Paul J. Killos
Attorney, Agent, or Firm—Y. Grace Tsang

[57] ABSTRACT

A catalyst system, which contains
a) a source of a Group VIII metal, and
b) a phosphine of general formula:

$$R^1-P-R^3 \quad\quad (I)$$
$$\underset{\underset{R^2}{|}}{}$$

in which $R^1$, $R^2$ and $R^3$ are independently selected from an optionally substituted aryl group and a group of general formula:

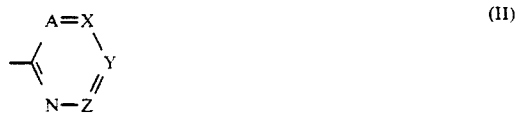

(II)

wherein each of A, X, Y and Z is independently selected from a nitrogen atom, a CH group and a group of formula CR wherein R represents a hydroxyl group, an amino group, an amido group, a cyano group, an aryl group, an aryloxy group, a halogen atom, an optionally substituted hydrocarbyl group or an optionally substituted hydrocarbyloxy group, it also being possible for two adjacent CR groups to form a ring, provided that at least one of $R^1$, $R^2$ and $R^3$ represents a group of formula (II) in which at least one of A and Z represents a group of formula CR; or an acid addition salt thereof.

Also disclosed is the use of the catalyst system in the selective carbonylation of unsaturated hydrocarbons.

11 Claims, No Drawings

CARBONYLATION CATALYST AND PROCESS

FIELD OF THE INVENTION

The present invention relates to a novel catalyst system comprising a phosphine, to certain novel phosphines, and to the use of the catalyst system in the carbonylation of olefins and acetylenes.

BACKGROUND OF THE INVENTION

Many processes are known in the art for the carbonylation of olefinically and acetylenically unsaturated compounds. A review of such processes is provided by J. Falbe, "New Syntheses with Carbon Monoxide", Springer-Verlag, Berlin Heidelberg New York, 1980. Typically the processes involve the reaction of an olefinically unsaturated compound with carbon monoxide and, in some cases, hydrogen or a nucleophilic compound having a removable hydrogen atom, in the presence of a carbonylation catalyst system. In many instances, the carbonylation catalyst system comprises a source of a Group VIII metal and a ligand such as a phosphine.

One type of catalyst system which has been disclosed in recent years comprises a source of a Group VIII metal and a pyridyl phosphine.

Kurti Kurtev et al, Journal of the Chemical Society, Dalton Transactions, 1980, pages 55 to 58, discloses catalyst systems comprising a rhodium or ruthenium compound and a pyridyl phosphine, and their use in the carbonylation of hex-1-ene.

U.S. Pat. No. 4,859,764, issued Aug. 22, 1989, discloses catalyst systems comprising a palladium compound, a pyridyl phosphine, an acid and a quinone and their use in the carbonylation of olefins to afford polymers.

European patent application publication number EP-A1-0271144, filed Nov. 25, 1987, discloses the use of catalyst systems comprising a palladium compound, a pyridyl phosphine and an acid in the carbonylation of acetylenes with hydroxyl-containing compounds.

U.S. Pat. No. 4,786,443, issued Nov. 22, 1988, discloses the use of catalyst systems comprising a palladium compound, a pyridyl phosphine and an acid in the carbonylation of olefins with hydroxyl-containing compounds.

None of the aforementioned references describes experiments in which a catalyst system comprising a (substituted-pyridyl)phosphine is used. However, European patent applications publication numbers U.S. Pat. No. 4,859,764, issued Aug. 22, 1989 and U.S. pat. No. 4,786,443, issued Nov. 22, 1988, contain lists of phosphines. All of the listed phosphines possess a heterocyclic substituent attached to phosphorus which is either unsubstituted or substituted with a halogen atom or an alkoxy group. No method is described for the preparation of any of these phosphines, nor are any physical characteristics of any of the phosphines provided. All of the phosphines described in the working examples possess an unsubstituted heterocyclic group attached to phosphorus.

Newkome et al, J. Am. Chem. Soc., 100 (17), 5567–8, discloses bis(6-ethoxy-2-pyridyl)phenyl phosphine, bis(6-chloro-2-pyridyl)phenyl phosphine, and bis(6-bromo-2-pyridyl)phenyl phosphine. It also discloses a bis(2-pyridyl)phenyl phosphine wherein the two 6-positions of the pyridyl groups are linked by a chain of formula $O(CH_2CH_2O)_5CH_2CH_2O$.

SUMMARY OF THE INVENTION

Surprisingly, it has now been found that beta-carbonylated products may be obtained with remarkably high selectivity when an alpha-unsaturated hydrocarbon, in particular propyne, is carbonylated using catalyst systems comprising certain (substituted-2-pyridyl) phosphines.

Accordingly, the present invention provides a catalyst system comprising a source of a Group VIII metal, and a phosphine of general formula:

in which $R^1$, $R^2$ and $R^3$ are independently selected from an optionally substituted aryl group and a group of general formula:

wherein each of A, X, Y and Z is independently selected from a nitrogen atom, a CH group and a group of formula CR, wherein R represents a hydroxyl group, an amino group, an amido group, a cyano group, an acyl group, an acyloxy group, a halogen atom, an optionally substituted hydrocarbyl group or an optionally substituted hydrocarbyloxy group, it also being possible for two adjacent CR groups to form a ring, provided that at least one of $R^1$, $R^2$ and $R^3$ represents a group of formula (II) in which at least one of A and Z represents a group of formula CR; or an acid addition salt thereof.

DETAILED DESCRIPTION OF THE INVENTION

Catalyst systems comprising a source of a Group VIII metal and a phosphine of general formula (I), or a salt thereof, have been found to produce beta-carboxylated products from alpha-unsaturated hydrocarbons, in particular propyne with substantially higher selectivity than corresponding phosphines of the same general formula (I) in which A and Z represent CH groups. Thus, methyl methacrylate has been prepared by reacting propyne, carbon monoxide and methanol with a selectivity of up to 99.9%, i.e. only 0.1% of by-products are formed. Each one-tenth of a percent improvement is worth millions of dollars in a large scale operation. Compared with the processes exemplified in the above-mentioned prior art, this represents a dramatic decrease in by-product formation. A high selectivity to the end product also means a high purity of the end product, so that little or no purification steps are necessary, and waste disposal problems are absent. Also, less catalyst poisoning and tar or gum formation in the reactor are encountered, so that generally the run times in continuous processes may be longer.

Without wishing to be bound by any theory, it is believed that the R groups present in the groups A and Z in the phosphines according to the invention exert a steric effect during the carbonylation of alpha-unsaturated compounds, thereby favouring the formation of beta-carbonylated products. Accordingly, it is believed that a wide range of unsaturated hydrocarbons may be selectively carbonylated using catalyst systems according to the invention.

Examples of groups represented by the general formula (II) are 2-pyridyl, 2-pyrazinyl, 2-quinolyl, 1-isoquinolyl, 3-isoquinolyl, 2-triazinyl, 2-pyrimidinyl, 3-pyridazinyl, 3-cinnolinyl, 2-quinoxalinyl and 2-quinazolinyl. Of these groups, 2-pyridyl is most preferred.

It has been found that catalyst systems according to the invention, wherein a group Z represents a group of formula CR confer the highest selectivity towards beta-carbonylated products. Accordingly, catalyst systems wherein a group Z, (especially each group Z) represents a group of formula CR, and acid addition salts thereof, are preferred.

Preferably at least one of A and Z in every group of general formula II represents a group of formula CR.

Preferably each of A, X and Y is independently selected from a CH group and a group of formula CR.

When reference is made in this specification to an optionally substituted group, the group is preferably substituted with one or more, for example one, two or three, substituents selected from a halogen atom, an alkyl group, a haloalkyl group, an alkoxy group and a haloalkoxy group.

Where reference is made to an amino group, it preferably means the group $NH_2$ or an alkyl or dialkylamino group.

An acyl group may be, for example, an alkanoyl group such as acetyl.

An amido group may be, for example, an acylamino group such as acetamido.

A ring formed by two adjacent CR groups is preferably an optionally substituted hydrocarbyl ring, for example an optionally substituted phenyl ring. Examples of $R^1$ groups having two adjacent CR groups which form a ring are quinolyl, isoquinolyl, quinoxalinyl and quinazolinyl.

When reference is made to an optionally substituted hydrocarbyl or hydrocarbyloxy group, the hydrocarbyl moiety preferably represents an alkyl group, a cycloalkyl group or a phenyl group.

An alkyl group preferably has up to 20 carbon atoms, more preferably up to 12 carbon atoms, especially from 1 to 4 carbon atoms. For example an alkyl group may be a methyl, ethyl, n-propyl, iso-propyl, n-butyl, iso-butyl or tert-butyl group.

A cycloalkyl group preferably has from 3 to 6 carbon atoms.

A halogen atom preferably means a fluorine, chlorine or bromine atom.

An aryl group is preferably a phenyl group.

Preferably each group R is independently selected from a halogen atom, a $C_{1-4}$ alkyl group and a $C_{1-4}$ alkoxy group. More preferably, each group R represents a $C_{1-4}$ alkyl group.

Most preferably, the phosphine of general formula (I) is a 6-substituted-2-pyridylphosphine, especially a 6-alkyl-2-pyridylphosphine.

Examples of phosphines of general formula (I) are: diphenyl(6-methoxy-2-pyridylphosphine, bis(6-ethoxy-2-pyridyl)phenylphosphine, bis(6-chloro-2-pyridyl)-phenylphosphine, bis(6-bromo-2-pyridyl)phenylphosphine, tris(6-methyl-2-pyridyl)phosphine, bis(6-methyl-2-pyridyl)phenylphosphine, bisphenyl(6-methyl-2-pyridyl)phosphine, bis(3-methyl-2-pyridyl)phenylphosphine, and bisphenyl(4,6-dimethyl-2-pyridyl)phosphine.

Preferred acid addition salts of the phosphines of general formula (I) include salts with sulfuric acid., a sulfonic acid, e.g. an optionally substituted hydrocarbylsulfonic acid such as an optionally substituted arylsulfonic acid, e.g. benzenesulfonic acid, p-toluenesulfonic acid or naphthalenesulfonic acid, an optionally substituted alkylsulfonic acid such as an alkylsulfonic acid, e.g. methanesulfonic acid or t-butylsulfonic acid, or a substituted alkyl sulfonic acid such as 2-hydroxypropanesulfonic acid. trifluoromethanesulfonic acid, chlorosulfonic acid or fluorosulfonic acid; a phosphonic acid, e.g. orthophosphonic acid, pyrophosphonic acid or benzenephosphonic acid; a carboxylic acid, e.g. chloroacetic acid, dichloroacetic acid, trichloroacetic acid, trifluoroacetic acid, oxalic acid or terephthalic acid; or a perhalic acid such as perchloric acid.

Examples of Group VIII metals are iron, cobalt, nickel, ruthenium, rhodium, palladium, iridium and platinum.

The catalyst system according to the invention preferably comprises a source of palladium.

The source of Group VIII metal may be, for example, the metallic element or a compound of the Group VIII metal. The source of a Group VIII metal is preferably a compound of the Group VIII metal, most preferably a compound of palladium.

Examples of compounds of Group VIII metals include salts, for example salts of nitric acid; sulfuric acid; carboxylic acids such as alkane carboxylic acids having not more than 12 carbon atoms, e.g. acetic acid; and hydrohalic acids. Other examples of salts are salts of the acids mentioned above in relation to the formation of acid addition salts by the phosphines of general formula (I). Since halide ions can be corrosive, salts of hydrohalic acids are not preferred. Other examples of compounds of Group VIII metals include complexes, such as complexes with acetylacetonate, phosphines (e.g. a phosphine of general formula I) and/or carbon monoxide. For example the compound of a Group VIII metal may be palladium acetylacetonate, tetrakis-triphenylphosphinepalladium, bis-tri-o-tolylphosphinepalladium acetate, bis-diphenyl-2-pyridylphosphinepalladium acetate, tetrakis-diphenyl-2-pyridylphosphinepalladium, bis-di-o-tolylpyridylphosphinepalladium acetate or bis-diphenylpyridylphosphinepalladium sulphate.

The number of moles of phosphine of general formula (I) per gram atom of Group VIII metal in the catalyst system according to the invention is not critical. It will depend upon the particular source of Group VIII metal and the particular reactants to be carbonylated. Conveniently the ratio of the number of moles of phosphine of general formula (I) per gram atom of Group VIII metal is in the range of from 1 to 1,000, preferably from 2 to 500, more preferably from 10 to 100.

The catalyst system according to the invention preferably further comprises a protonic acid. The function of the protonic acid is to provide a source of protons. Accordingly, the protonic acid may be generated in situ. Preferably the protonic acid is one of those referred to hereinabove in relation to the formation of acid addition salts by the phosphines of general formula (I). It may also be, for example, an acidic ion exchange resin, for example a sulphonated ion exchange resin.

It will be appreciated that a catalyst system comprising an acid addition salt of a phosphine of general formula (I), inevitably comprises a protonic acid.

The catalyst system preferably comprises a non-coordinating anion; that is to say an anion which does not coordinate with the Group VIII metal. Conveniently the non-coordinating anion is derived from the protonic acid. The protonic acids listed above in relation to the formation of acid addition salts by the phosphines of general formula (I) comprise non-coordinating anions.

When the catalyst system comprises a protonic acid, the ratio of the number of equivalents of protonic acid per equivalent of phosphine of general formula (I) may vary over a wide range. The optimal ratio of protonic acid to phosphine of general formula (I) will depend upon the particular reaction in which the catalyst composition is to be used. Conveniently the number of equivalents of protonic acid per equivalent of phosphine of general formula (I) will be in the range of from 0.1 to 50, preferably from 0.5 to 5.

The catalyst system according to the invention is constituted in a liquid phase. The liquid phase may conveniently be formed by one or more of the reactants with which the catalyst system is to be used. Alternatively, it may be formed by a solvent. It may also be formed by one of the components of the catalyst system.

The catalyst system according to the invention may be homogeneous or heterogeneous. Most preferably it is homogeneous.

The catalyst system according to the invention may be generated by any convenient method. Thus it may be prepared by combining a Group VIII metal compound, a phosphine of general formula (I) and, if appropriate, a protonic acid, in a liquid phase. Alternatively, it may be prepared by combining a Group VIII metal compound and an acid addition salt of general formula (I) in a liquid phase. Alternatively, it may be prepared by combining a Group VIII metal compound which is a complex of a Group VIII metal with a phosphine of general formula (I), and if appropriate, a protonic acid, in a liquid phase.

As has been stated above three phosphines of general formula (I) have been disclosed in Newkome et al, *J. Amer. Chem. Soc.*, 100 (17), 5567–8. Several other phosphines have been named in U.S. Pat. Nos. 4,859,764 and 4,786,443, but their preparation has not been described. These phosphines are accordingly believed to be novel. The invention therefore provides a phosphine of general formula (I) or an acid addition salt thereof as defined above, except for bis(6-ethoxy-2-pyridyl)phenyl phosphine, bis(6-chloro-2-pyridyl)phenyl phosphine, and bis(6-bromo-2-pyridyl)phenyl phosphine.

The phosphines of general formula (I) which have been referred to previously are all compounds in which at least one A or Z represents a group of formula CR where R represents a halogen atom or an alkoxy group. Unexpectedly, it has been found that phosphines of general formula (I) wherein a group A and/or Z may be represented by the formula CR in which R represents an optionally substituted hydrocarbyl group possess advantageous properties compared with corresponding phosphines of formula (I) with halogen or alkoxy substituents. In particular, in the preparation of methylmethacrylate by the reaction of propyne with carbon monoxide and methanol, such compounds have been found to be associated with a substantially higher reaction rate than corresponding alkoxy and halo-substituted compounds, whilst still affording a very high selectivity.

According to a preferred aspect therefore; the invention provides phosphines of the general formula (I) in which at least one of A and Z represent a group of formula CR, wherein R represents an optionally substituted hydrocarbyl group. Preferably Z represents a group of formula CR wherein R represents an optionally substituted hydrocarbyl group, preferably an alkyl group.

The phosphines of general formula (I) may be prepared by a process which comprises reacting a compound of general formula:

in which $M^1$ represents either a metal atom or a leaving atom or group, with an appropriate compound of general formula:

in which $M^2$ represents either a metal atom or a leaving atom or group, optionally followed by forming an acid addition salt.

A metal atom represented by $M^1$ or $M^2$ may be any main group metal, for example an alkali metal, such as lithium, sodium or potassium; an alkaline earth metal, such as magnesium; zinc; cadmium; mercury; aluminium, gallium, indium, thallium, tin or lead. Preferably a metal atom is an alkali metal atom, most preferably a lithium atom.

It will be appreciated that when $M^1$ represents a metal atom, the appropriate compound of general formula (IV) is one wherein $M^2$ represents a leaving atom or group. Similarly when $M^1$ represents a leaving atom or group, the appropriate compound of general formula (IV) is one wherein $M^2$ represents a metal atom.

Preferably $R^1$ represents a group of general formula (II) as defined above.

The reaction between the compound of general formula (III) with the compound of general formula (IV) may conveniently be effected in the presence of a solvent. Suitable solvents include liquid ammonia and ethers such as tetrahydrofuran or diethyl ether, or hydrocarbons such as benzene or toluene.

The process is conveniently effected at a temperature in the range of from $-100°$ to $100°$ C., preferably from $-80°$ to $0°$ C.

Where a compound of general formula (I) is desired wherein more than one of $R^1$, $R^2$ and $R^3$ represents a group of formula (II), the starting material of formula (III) may be generated in situ from the appropriate phosphine. For example, when a compound of formula (I) is desired wherein each of $R^1$, $R^2$ and $R^3$ represents a group of formula (II), the starting material of formula (III) may be generated in situ from a compound of formula:

wherein each $M^1$ represents a leaving atom or group, preferably a chlorine or bromine atom.

The compounds of formula (IV) wherein $M^2$ represents a metal atom may be prepared from the corresponding compounds wherein $M^2$ represents a leaving atom or group, for example a chlorine, bromine or iodine atom by reaction with a metal alkyl, for example butyl lithium.

An acid addition salt may conveniently be formed by contacting a phosphine of general formula (I) with an appropriate acid, preferably in the presence of a solvent.

As has been stated above, it has surprisingly been found that compositions according to the invention are highly selective in the carbonylation of unsaturated hydrocarbons.

Accordingly, the invention further provides the use of a catalyst composition as defined hereinbefore in the carbonylation of an acetylenically or olefinically unsaturated hydrocarbon.

According to another aspect, the invention provides a process for the carbonylation of an acetylenically or olefinically unsaturated compound, which comprises reacting an acetylenically or olefinically unsaturated compound in a liquid phase with carbon monoxide in the presence of a catalyst system as defined above.

The acetylenically or olefinically unsaturated compound is preferably an asymmetric acetylene or olefin, most preferably an alpha acetylene or olefin.

An olefinically unsaturated compound is preferably a substituted or unsubstituted alkene or cycloalkene having from 2 to 30, preferably from 3 to 20 carbon atoms per molecule.

An acetylenically unsaturated compound is preferably a substituted or unsubstituted alkyne having from 2 to 20, especially from 3 to 10 carbon atoms per molecule.

The acetylenically or olefinically unsaturated compound may contain one or more acetylenic or olefinic bonds, for example one, two or three acetylenic or olefinic bonds.

An olefin or acetylene may be substituted by, for example, a halogen atom, a cyano group, an acyl group such as acetyl, an acyloxy group such as acetoxy, an amino group such as dialkylamino, an alkoxy group such as methoxy, a haloalkyl group such as trifluoromethyl, a haloalkoxy group such as trifluoromethoxy, an amido group such as acetamido, or a hydroxy group. Some of these groups may take part in the reaction, depending upon the precise reaction conditions. For example, lactones may be obtained by carbonylating certain acetylenically unsaturated alcohols, for example 3-butyn-1-ol, 4-pentyn-1-ol or 3-pentyn-1-ol. Thus 3-butyn-1-ol may be converted into a-methylene-c-butyrolactone.

Examples of alkynes are: ethyne, propyne, phenylacetylene, 1-butyne, 2-butyne, 1-pentyne, 1-hexyne, 1-heptyne, 1-octyne, 2-octyne, 4-octyne, 1,7-octadiyne, 5-methyl-3-heptyne, 4-propyl-2-pentyne, 1-nonyne, benzylethyne and cyclohexylethyne.

Examples of alkenes are: ethene, propene, phenylethene, 1-butene, 2-butene, 1-pentene, 1-hexene, 1-heptene, 1-octene, 2-octene, 4-octene, cyclohexene and norbornadiene.

The acetylenically or olefinically unsaturated compound can be both an acetylene and an olefin, for example as in 3-methyl-but-3-ene-2-yne.

It has been found that catalyst systems according to the invention are highly selective for acetylenic groups in the presence of olefinic groups.

The unsaturated compound may be carbonylated alone or in the presence of other reactants, for example, hydrogen or a nucleophilic compound having a removable hydrogen atom. An example of a nucleophilic compound having a removable hydrogen atom is a hydroxyl-containing compound.

A hydroxyl-containing compound is preferably an alcohol, water or a carboxylic acid.

Any alcohol used may be aliphatic, cycloaliphatic or aromatic and may carry one or more substituents. The alcohol preferably comprises up to 20 carbon atoms per molecule. It may be, for example, an alkanol, a cycloalkanol or a phenol. One or more hydroxyl groups may be present, in which case several products may be formed, depending on the molar ratio of the reactants used.

Examples of alkanols include methanol, ethanol, 1-propanol, 2-propanol, 1-butanol, 2-butanol, 2-methylpropan-1-ol, and 2-methylpropan-2-ol.

Examples of phenols include phenol, alkylphenols, catechols, and 2,2-bis(4-hydroxyphenyl)propane.

Other examples of alcohols include polyvalent alcohols, in particular lower sugars such as glucose, fructose, mannose, galactose, sucrose, aldoxose, aldopentose, altrose, allose, talose, gulose, idose, ribose, arabonose, xylose, lyxose, erythrose or threose, cellulose, benzyl alcohol, 2,2-bis(hydroxymethyl)-1-butanol, stearyl alcohol, cyclohexanol, ethylene glycol, 1,2-propanediol, 1,4-butanediol, polyethyleneglycol, glycerol and 1,6-hexanediol.

The process according to the present invention can be carried out using a wide variety of carboxylic acids. For example, the carboxylic acids may be aliphatic, cycloaliphatic or aromatic and may carry one or more substituents, such as those named in connection with the acetylenically and olefinically unsaturated compounds.

Carboxylic acids preferably used in the process according to the invention include those containing up to 20 carbon atoms. One or more carboxylic acid groups may be present, thus allowing various products as desired, depending on the molar ratio of the reactants used. The carboxylic acids may, for example, be alkanecarboxylic acids or alkenecarboxylic acids. Examples of carboxylic acids are: formic acid, acetic acid, propionic acid, n-butyric acid, isobutyric acid, pivalic acid, n-valeric acid, n-caproic acid, caprylic acid, capric acid, lauric acid, myristic acid, palmitic acid, stearic acid, benzoic acid, o-phthalic acid, m-phthalic acid, terephthalic acid and toluic acid. Examples of alkenecarboxylic acids are acrylic acid, propiolic acid, methacrylic acid, crotonic acid, isocrotonic acid, oleic acid, maleic acid, fumaric acid, citraconic acid and mesaconic acid.

It will be appreciated that the unsaturated hydrocarbon and the hydroxyl-containing compound may be the same compound.

When an acetylenically unsaturated compound is reacted with water and carbon monoxide, an alpha,-beta-unsaturated carboxylic acid is formed. If an alcohol is used instead of water, an alpha,beta-unsaturated carboxylic ester is formed. If a carboxylic acid is used instead of water, an alpha,beta-unsaturated anhydride is formed. The alpha,beta-unsaturated product may undergo further reaction depending upon the reaction conditions employed.

It has been found that compositions according to the invention are particularly useful for the carbonylation of alpha acetylenes with hydroxyl-containing compounds.

Accordingly, to a preferred aspect, therefore, the invention provides a process for the preparation of an alpha,beta-olefinically unsaturated compound, which comprises reacting an alpha acetylene with carbon monoxide and a hydroxyl-containing compound in the liquid phase in the presence of a carbonylation catalyst as hereinbefore described.

In the process, the carbonylation catalyst is preferably a palladium catalyst as described above, namely a catalyst which comprises:
a) a palladium compound,
b) a phosphine of general formula (I), and
c) a protonic acid.

It is not essential to use a separate solvent in the process according to the invention.

A large excess of the product or of one of the reactants, for example an alcohol, can often form a suitable liquid phase. In some cases, however, it may be desirable to use a separate solvent. Any inert solvent can be used for that purpose. Said solvent may, for example, comprise sulfoxides and sulfones, for example dimethylsulfoxide, diisopropylsulfone or tetrahydrothiophene-2,2-dioxide (also referred to as sulfolane), 2-methylsulfolane, 3-methylsulfolane, 2-methyl-4-butylsulfolane; aromatic hydrocarbons such as benzene, toluene, xylenes; esters such as methylacetate and butyrolactone; ketones such as acetone or methyl isobutyl ketone, ethers such as anisole, 2,5,8-trioxanonane (also referred to as diglyme), diphenyl ether and diisopropyl ether, and anides such as N,N-dimethylacetamide or N-methylpyrrolidone.

The process according to the present invention is conveniently effected at a temperature in the range of from 10° C. to 200° C., in particular from 20° C. to 100° C.

The process according to the invention is preferably effected at a pressure of from 1 to 70 bar. Pressures higher than 100 bar may be used, but are generally economically unattractive on account of special apparatus requirements.

The molar ratio of the hydroxyl-containing compound to the unsaturated hydrocarbon may vary between wide limits and generally lies within the range of 0.01:1 to 100:1.

The quantity of the Group VIII metal is not critical. Preferably, quantities are used within the range of $10^{-7}$ to $10^{-1}$ gram atom Group VIII metal per mol of unsaturated compound.

The carbon monoxide required for the process according to the present invention may be used in a practically pure form or diluted with an inert gas, for example nitrogen. The presence of more than small quantities of hydrogen in the gas stream is undesirable on account of the hydrogenation of the unsaturated hydrocarbon which may occur under the reaction conditions. In general, it is preferred that the quantity of hydrogen in the gas stream supplied is less than 5 vol %.

The selectivity towards alpha,beta-olefinically unsaturated compounds, expressed as a percentage, is defined as $(a/b) \times 100$ wherein "a" is the quantity of acetylenically unsaturated compound converted into alpha,beta-olefinically unsaturated compound and "b" is the total quality of acetylenically unsaturated compound that has been converted.

The invention will now be illustrated by the following Preparations and Examples.

Unless otherwise stated, the allene content of any propyne used in the following examples was less than 0.2%.

PREPARATION 1

Preparation of diphenyl-(6-methyl-2-pyridyl)-phosphine

All manipulations were carried out in an inert atmosphere (nitrogen or argon). Solvents were dried and distilled prior to use. 36 ml of a 1.6M n-butyllithium solution in hexane was added to 40 ml diethyl ether, and the mixture was cooled to −40° C. To the stirred mixture was added in the course of 20 minutes a solution of 10 g 2-bromo-6-methylpyridine in 15 ml diethyl ether; during this addition, the temperature was kept at −40° C. After the addition, the temperature was raised to −5° C., kept there for 5 minutes, and then lowered again to −40° C. A solution of 12.8 g chlorodiphenylphosphine in 15 ml diethyl ether was added in the course of 15 minutes to the stirred mixture. After the addition, the mixture was warmed to room temperature, the solvents were removed in vacuo, and 50 ml water and 50 ml dichloromethane were added. After 5 minutes of vigorous stirring, the dichloromethane layer was separated. The water layer was extracted with two 50 ml portions of dichloromethane, the organic reactions were combined, and the solvent removed in vacuo. The residue was crystallized from toluene/hexane to afford 12 g (75%) of diphenyl-(6-methyl-2-pyridyl)-phosphine as off-white crystals. The product was characterized by $^{31}P$ NMR: $d_q = -5.6$ ppm.

PREPARATION 2

Preparation of diphenyl-(3-methyl-2-pyridyl)-phosphine

This compound was prepared as described in preparation 1, but using 10.0 g 2-bromo-3-methylpyridine instead of the 2-bromo-6-methylpyridine. It was characterized by $^{31}P$ NMR: $d_q = -8.1$ ppm.

PREPARATION 3

Preparation of phenyl-bis(6-methyl-2-pyridyl)-phosphine

This compound was prepared as described in preparation 1, but using 5.2 g phenyldichlorophosphine instead of the chlorodiphenylphosphine. It was characterized by $^{31}P$ NMR: $d_q = -5.1$ ppm.

PREPARATION 4

Preparation of tris(6-methyl-2-pyridyl)-phosphine

This compound was prepared as described in preparation 1, but using 2.7 g phosphorus trichloride instead of the chlorodiphenylphosphine. It was characterized by $^{31}P$ NMR: $d_q = -3.8$ ppm.

PREPARATION 5

Preparation of diphenyl-(4,6-dimethyl-2-pyridyl)-phosphine

This compound was prepared as described in preparation 1, but using 10.8 g 2-bromo-4,6-dimethylpyridine instead of the 2-bromo-6-methylpyridine. It was characterized by $^{31}P$ NMR: $d_q = -5.6$ ppm.

PREPARATION 6

Preparation of diphenyl-(6-methoxy-2-pyridyl)-phosphine 2.7 g Sodium was added to 100 ml liquid ammonia at −80 °C., and then 15.2 g triphenylphosphine was added in 6 portions with stirring. The solution was slowly warmed to −40° C., kept at that temperature for 30 min, and then cooled again to −80° C. Then, 3.1 g ammonium chloride was added to the stirred solution, followed by 10.9 g 2-bromo-6-methoxypyridine in three portions. The cooling bath was removed and the ammonia was allowed to evaporate. The residue was worked up with water/dichloromethane as described in preparation 1. Crystallization from hexane afforded 7 g of a somewhat impure product (characterized by $^{31}$P NMR: $d_q = -4.4$ ppm) which was used as such in the following Examples.

EXAMPLE 1

A 300 ml magnetically stirred stainless steel autoclave was successively filled with 0.025 mmol palladium(II) acetate, 1 mmol bis(6-methyl-2-pyridyl)phenylphosphine, 2 mmol paratoluenesulfonic acid, 30 ml N-methylpyrrolidone and 30 ml methanol. Air was evacuated from the autoclave, whereupon 25 ml propyne was added. Subsequently, carbon monoxide was added to a pressure of 60 bar. The autoclave was sealed and heated to a temperature of 80° C. After a reaction time of 1.5 hours at 80° C. a specimen of the contents was analysed by means of gas liquid chromatography. The selectivity of the conversion of propyne to methyl methacrylate was found to be 99.9% while the mean conversion rate was calculated to be 20,000 mol propyne/gat Pd/hour.

EXAMPLE 2

The experiment as described in Example 1 was repeated in substantially the same manner with a catalyst system composed of 0.025 mmol palladium(II) acetate, 1 mmol tris(6-methyl-2-pyridyl)- phosphine and 2 mmol paratoluenesulfonic acid. The selectivity of propyne conversion to methyl methacrylate amounted to 99.8% and the mean conversion rate was 10,000 mol propyne/gat Pd/hour.

EXAMPLE 3

The procedure of Example 1 was repeated, except that a catalyst system composed of 0.025 mmol palladium(II) acetate, 1 mmol bisphenyl(6-methyl-2-pyridyl)-phosphine and 2 mmol paratoluenesulfonic acid was used, the autoclave was heated to 60° C. and the contents of the autoclave were analysed after a reaction time of 1 hour. The selectivity of the conversion to methyl methacrylate was found to be 99.95%. The mean conversion rate was calculated to be 40,000 mol propyne/gat Pd/hour.

EXAMPLE 4

A 300 ml magnetically stirred steel autoclave was filled with 0.025 mmol palladium(II) acetate, 3 mmol bisphenyl(6-methyl-2-pyridyl)phosphine, 2 mmol paratoluenesulfonic acid and 50 ml methanol. Air was evacuated from the autoclave, and then 30 ml propylene was added. The autoclave was then pressurized to 40 bar with carbon monoxide. The autoclave was sealed and heated to a temperature of 100° C. Analysis of the reaction product showed a selectivity to beta-carbonylated product of 36%, and a mean conversion rate of 500 mol/gat Pd/hour.

EXAMPLE 5

The method of Example 4 was repeated, but using bisphenyl(6-methoxy-2-pyridyl)phosphine. The selectivity was found to be 39%, and the mean conversion rate 600 mol/gat Pd/hour.

COMPARATIVE EXAMPLE A

The experiment as described in Example 1 was repeated in a virtually analogous manner with a catalyst system composed of 0.025 mmol palladium(II) acetate, 1 mmol phenyl-di(2-pyridyl)phosphine and 2 mmol paratoluenesulfonic acid, a reaction temperature of 80° C. and a reaction time of 2 hours. The selectivity of propyne to methyl methacrylate conversion amounted to 98.3% (compared with 99.9% in Example 1), while the mean conversion rate was now calculated to be 8,000 mol propyne/gat Pd/hour.

Accordingly, the experiment demonstrates the surprising advantage of using a substituted pyridylphosphine according to the invention.

COMPARATIVE EXAMPLE B

The method of Example 4 was repeated, but using bisphenyl(2-pyridyl)phosphine. The selectivity to beta-carbonylated product was only 28%, with a mean conversion rate of 270 mol/gat Pd/hour.

This comparative example demonstrates that the phosphines according to the invention are useful for the selective carbonylation of olefins.

EXAMPLE 6

A 250 ml magnetically-stirred stainless steel autoclave was successively filled with 0.025 mmol palladium(II)acetate, 1 mmol bisphenyl (6-methyl-2-pyridyl) phosphine, 2 mmol 2-methyl-2-propylsulfonic acid, 30 ml N-methylpyrrolidone as solvent and 30 ml methanol. Air was then evacuated from the autoclave, and then 30 ml propyne containing 0.2% allene was added. Carbon monoxide was then added to a pressure of 60 bar. The autoclave was then sealed and heated to a temperature of 60° C. After a reaction time of 0.15 hours at 60° C., a sample of the contents of the autoclave was analyzed by gas liquid chromatography. From the results of the analysis the selectivity to methylmethacrylate was calculated to be 99.95%, and the mean conversion rate was calculated to be 100,000 mol propyne/gram atom Pd/hour.

EXAMPLES 7 TO 17 AND COMPARATIVE EXAMPLES C TO E

The method of Example 1 was repeated using differing acids, solvents and phosphines, and differing amounts of allene in the propyne. The results are summarized in Table 1.

TABLE 1

Carbonylation of Propyne and Methanol to give methyl methacrylate

| Example | Ligand (mmol) | Acid (mmol) | Solvent | % allene | Temp (°C) | Selectivity % | Mean Conversion rate (mol propyne/gat.Pd/hr) |
|---|---|---|---|---|---|---|---|
| 6 | 2-(CH₃)-6-(Pφ₂)-pyridine (1) | (CH₃)₃CSO₃H (2) | NMP | 0.2 | 60 | 99.95 | 100,000 |
| 7 | 2-(CH₃)-6-(Pφ₂)-pyridine (1) | (CH₃)SO₂H (2) | NMP | 0.2 | 60 | 99.95 | 50,000 |
| C | 2-(Pφ₂)-pyridine (1) | CH₃-C₆H₄-SO₃H (2) | NMP | 0.2 | 60 | 98.9 | 40,000 |
| 8 | 2-(Pφ₂)-pyridine (1) | C₆H₅-PO₃H₂ (10) | NMP | 0.2 | 60 | 99.95 | 6,000 |
| 9 | 2-(CH₃)-6-(Pφ₂)-pyridine (1) | CF₃SO₃H (2) | NMP | 0.2 | 60 | 99.95 | 16,000 |
| 10 | 2-(CH₃)-6-(Pφ₂)-pyridine (1) | CF₃COOH (10) | NMP | 0.2 | 60 | 99.95 | 14,000 |
| 11 | 2-(CH₃)-6-(Pφ₂)-pyridine (1) | (CH₃)₃CSO₃H (2) | NMP | 0.4 | 60 | 99.95 | 10,000 |
| 12 | 2-(CH₃)-6-(Pφ₂)-pyridine (1) | (CH₃)₃CSO₃H (2) | NMP | 0.4 | 70 | 99.95 | 50,000 |
| 13 | 2-(CH₃)-6-(Pφ₂)-pyridine (1) | CH₃SO₃H (2) | DMA | 0.4 | 60 | 99.95 | 45,000 |
| 14 | 2-(CH₃)-6-(Pφ₂)-pyridine (1) | CH₃SO₃H (2) | MMA | 0.4 | 60 | 99.95 | 5,000 |

TABLE 1-continued

Carbonylation of Propyne and Methanol to give methyl methacrylate

| Example | Ligand (mmol) | Acid (mmol) | Solvent | % allene | Temp (°C.) | Selectivity % | Mean Conversion rate (mol propyne/gat.Pd/hr) |
|---|---|---|---|---|---|---|---|
| D | 2-(diphenylphosphino)pyridine (1) | $CH_3SO_3H$ (2) | MMA | 0.4 | 60 | 98.9 | 7,000 |
| 15 | 2-(diphenylphosphino)-3-methylpyridine (1) | $CH_3SO_3H$ (2) | NMP | 0.4 | 70 | 99.2 | 12,000 |
| E | 2-(diphenylphosphino)-4-methylpyridine (1) | $CH_3SO_3H$ (2) | NMP | 0.4 | 70 | 98.8 | 8,000 |
| 16 | 2-(diphenylphosphino)-4,6-dimethylpyridine (1) | $CH_3SO_3H$ (2) | NMP | 0.4 | 70 | 99.9 | 11,000 |
| 17 | 2-(diphenylphosphino)-6-methoxypyridine (1) | $CH_3SO_3H$ (2) | NMP | 0.4 | 80 | 99.85 | 3,500 |

Key
NMP N-methylpyrrolidone
DMA N,N-dimethylacetamide
MMA Methylmethacrylate
φ Phenyl group

EXAMPLE 18

A 250 ml magnetically-stirred stainless steel autoclave was filled with 0.025 mmol palladium(II)acetate, 3 mmol bisphenyl (6-methyl-2-pyridyl) phosphine, 2 mmol 2-methyl-2-propylsulfonic acid, 30 ml methanol and 30 ml phenylacetylene. Air was then evacuated from the autoclave. Carbon monoxide was then added to a pressure of 60 bar. The autoclave was then sealed and heated to a temperature of 60° C. After a reaction time of 1 hour, a sample of the contents of the autoclave was analyzed by gas liquid chromatography. From the results of the analysis, the selectivity to methyl 2-phenylprop-2-enoate was 99.9% and the mean conversion rate was calculated to be 20,000 mol phenylacetylene/gram atom Pd/hour.

EXAMPLES 19 TO 22

Following a method similar to that described in Example 18, experiments were performed using various acetylenically unsaturated compounds. The results are given in Table 2.

TABLE 2

| Example | Acetylene (ml) | Ligand (mmol) | Acid (mmol) | Methanol (ml) | Solvent | Pd(OAc)₂ (mmol) | Temp (°C.) | Time (h) | Product | Mean conversion rate (mol propyne/gat.Pd.hr) | Selectivity % |
|---|---|---|---|---|---|---|---|---|---|---|---|
| 19 | HC≡C—(CH₂)₆C≡CH (10) | [pyridine with Pφ₂ and CH₃, (3)] | CH₃SO₃H (2) | 30 | — | 0.025 | 60 | 3 | CH₂=C—(CH₂)₄—C=CH₂ with COOCH₃ groups | 10,000 | >95% |
| 20 | CH₃-C(CH₂)=C≡CH (10) | [pyridine with Pφ₂ and CH₃, (3)] | CH₃SO₃H (1) | 40 | — | 0.1 | 45 | 2 | CH₃ / CH₂=C—C=CH₂ / COOCH₃ | 5,000 | >90%* |
| 21 | CH₃CH=CH₂ (50) / CH₃C≡CH (20) | [pyridine with Pφ₂ and CH₃, (3)] | CH₃SO₃H (1) | 30 | MMA** 30 | 0.025 | 60 | 1 | CH₃ / H₂C=C—COOCH₃ | 50,000 | 99.95 |
| 22 | HC≡C—CH₂CH₂OH*** (10g) | [pyridine with Pφ₂ and CH₃ (3); p-CH₃-C₆H₄-SO₃H (3)] | | — | Toluene 40 | 0.1 | 60 | <0.2 | H₂C=C—CH₂—CH₂—O—C=O (lactone) | 15,000 | >99% |

*60% conversion
**Methylmethacrylate
***20 mg hydroquinone present

EXAMPLE 23

A 300 ml magnetically stirred stainless steel autoclave was successively filled with 0.025 nmol palladium(II) acetate, 1 nmol bis(6-methyl-2-pyridyl)phenylphosphine, 2 nmol paratoluenesulfonic acid, 30 ml N-methylpyrrolidone and 30 ml methanol. Air was evacuated from the autoclave, whereupon 25 ml propyne was added. Subsequently, carbon monoxide was added to a pressure of 60 bar. The autoclave was sealed and heated to a temperature of 80° C. After a reaction time of 1.5 hours at 80° C. a specimen of the contents was analysed by means of gas liquid chromatography. The selectivity of the conversion of propyne to methyl methacrylate was found to be 99.9% while the mean conversion rate was calculated to be 20,000 mol propyne/gat Pd/hour.

EXAMPLE 24

The experiment as described in Example 23 was repeated in substantially the same manner with a catalyst system composed of 0.025 nmol palladium(II) acetate, 1 nmol tris(6-methyl-2-pyridyl)-phosphine and 2 nmol paratoluenesulfonic acid. The selectivity of propyne conversion to methyl methacrylate amounted to 99.8% and the mean conversion rate was 10,000 mol propyne/gat Pd/hour.

EXAMPLE 25

Comparative

The experiment as described in Example 23 was repeated in a virtually analogous manner with a catalyst system composed of 0.025 nmol palladium(II) acetate, 1 nmol phenyl-di(2-pyridyl)phosphine and 2 nmol paratoluenesulfonic acid, a reaction temperature of 80° C. and a reaction time of 2 hours. The selectivity of propyne to methyl methacrylate conversion amounted to 98.3%, while the mean conversion rate was calculated to be 8,000 mol propyne/gat Pd/hour.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention as defined by the instant specification and claims.

What is claimed is:

1. A catalyst system, which comprises
   a) a Group VIII metal, and
   b) a phosphine of the following formula or an acid addition salt thereof:

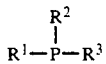

(I)

in which $R^1$, $R^2$ and $R^3$ are independently selected from an optionally substituted aryl group and a group of general formula:

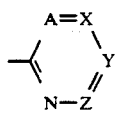

(II)

wherein each of A, X, Y and Z is independently selected from a CH group and a group of formula CR; wherein R represents a hydroxyl group, an amino group, an amido group, a cyano group, an acyl group, an acyloxy group, a halogen atom, an optionally substituted hydrocarbyl group or an optionally substituted hydrocarbyloxy group, it also being possible for two adjacent CR groups to form a ring; wherein at least one of $R^1$, $R^2$ and $R^3$ represents a group of formula II; wherein at least one of A and Z represents a group of formula CR wherein R is an optionally substituted alkyl group.

2. The catalyst system as claimed in claim 1, in which the group Z represents a group of formula CR wherein R represents an optionally substituted alkyl group.

3. The catalyst system as claimed in claim 1, in which the Group VIII metal is obtained from a compound of palladium.

4. The catalyst system as claimed in claim 2, in which the Group VIII metal is obtained from a compound of palladium.

5. The catalyst system as claimed in claim 4, in which the number of moles of phosphine per gram atom of palladium metal is in the range of from about 2 to about 500.

6. The catalyst system as claimed in claim 5, in which a protonic acid is present in an amount in the range of from about 0.5 to about 5 equivalents per equivalent of phosphine.

7. The catalyst system as claimed in claim 4, wherein the R is an alkyl group with one to four carbon atoms.

8. The catalyst system as claimed in claim 4, in which the phosphine is bisphenyl(6-methyl-2-pyridyl)phosphine.

9. The catalyst system as claimed in claim 4, in which the phosphine is tris(6-methyl-2-pyridyl)phosphine.

10. The catalyst system as claimed in claim 4, in which the phosphine is bis(6-methyl-2-pyridyl)phenyl phosphine.

11. A catalyst system which comprises
    a) a palladium compound,
    b) bisphenyl(6-methyl-2-pyridyl)phosphine, and
    c) from about 0.5 to about 5 equivalents of a sulfonic acid per equivalent of the phosphine in (b).

* * * * *